United States Patent
Follman et al.

(10) Patent No.: US 7,534,230 B2
(45) Date of Patent: May 19, 2009

(54) SYSTEMS AND METHODS FOR ADMINISTERING A MEDICAL REGIMEN

(75) Inventors: Mark Follman, Glen Rock, NJ (US); Ray Yao, Tarrytown, NY (US); Scott Gisler, Allendale, NJ (US); Victor Chan, Landing, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 72 days.

(21) Appl. No.: 11/554,138

(22) Filed: Oct. 30, 2006

(65) Prior Publication Data

US 2007/0239116 A1 Oct. 11, 2007

Related U.S. Application Data

(63) Continuation of application No. PCT/US2005/014041, filed on Apr. 25, 2005.

(60) Provisional application No. 60/566,976, filed on Apr. 30, 2004.

(51) Int. Cl.
*A61M 5/00* (2006.01)
*A61M 31/00* (2006.01)

(52) U.S. Cl. ............ 604/187; 604/65; 604/189

(58) Field of Classification Search ............ 604/187, 604/189, 65; 206/571
See application file for complete search history.

(56) References Cited

U.S. PATENT DOCUMENTS

| | | | | |
|---|---|---|---|---|
| 685,091 A | * | 10/1901 | Becton | 206/365 |
| 1,625,035 A | * | 4/1927 | Lilly | 206/571 |
| 3,723,061 A | * | 3/1973 | Stahl | 206/370 |
| 5,536,249 A | | 7/1996 | Castellano et al. | |
| 5,593,390 A | | 1/1997 | Castellano et al. | |
| 5,728,074 A | * | 3/1998 | Castellano et al. | 604/207 |
| 5,925,021 A | | 7/1999 | Castellano et al. | |
| D425,990 S | | 5/2000 | Gravel et al. | |
| 6,192,891 B1 | * | 2/2001 | Gravel et al. | 604/187 |
| 6,277,099 B1 | | 8/2001 | Strowe et al. | |
| 6,302,855 B1 | | 10/2001 | Lav et al. | |
| 6,540,672 B1 | | 4/2003 | Simonsen et al. | |
| 6,558,320 B1 | | 5/2003 | Causey, III et al. | |
| 6,781,522 B2 | * | 8/2004 | Sleva et al. | 340/870.1 |
| 6,875,195 B2 | | 4/2005 | Choi | |
| 2002/0013522 A1 | | 1/2002 | Lav et al. | |
| 2005/0182358 A1 | * | 8/2005 | Veit et al. | 604/93.01 |

FOREIGN PATENT DOCUMENTS

| | | |
|---|---|---|
| EP | 0 519 137 A1 | 12/1992 |
| WO | WO 01/59570 A1 | 8/2001 |
| WO | WO 02/092153 A2 | 11/2002 |
| WO | WO 03/005891 A1 | 1/2003 |
| WO | WO 03/015838 A2 | 2/2003 |

* cited by examiner

*Primary Examiner*—Kevin C Sirmons
*Assistant Examiner*—Bhisma Mehta
(74) *Attorney, Agent, or Firm*—Woodard, Emhardt, Moriarty, McNett & Henry LLP

(57) ABSTRACT

A medical regimen can be administered with a diagnostic and medication delivery system. In one form the system includes a medication delivery pen with a controller and a monitor for monitoring a characteristic of a bodily fluid with a controller. A case includes a compartment for removably storing the medication delivery pen and the monitor. The case includes a communications link for establishing communication between the controller of the pen and the controller of the monitor. The medication delivery pen and monitor are operable in a first mode cooperative with one another and in a second mode independent of one another.

17 Claims, 7 Drawing Sheets

SYSTEMS AND METHODS FOR ADMINISTERING A MEDICAL REGIMEN

REFERENCE TO RELATED APPLICATIONS

This application is a continuation of International Application No. PCT/US2005/014041 filed Apr. 25, 2005 (which was published in English), which claims the benefit of U.S. patent application Ser. No. 60/566,976 filed Apr. 30, 2004, which is hereby incorporated by reference in its entirety.

BACKGROUND

There are known various devices which measure, record and receive input data relating to a bodily characteristic or administration of treatment. These devices can store the data for review on a display of the device, or for subsequent transfer to a computer or other device which facilitates the review and analysis of the uploaded data.

For persons with medical conditions requiring a measurement device and an administration device, each device can be employed independently of one another to maintain the recorded data separately in each device. Inconvenience is created by having to review and transfer the recorded data from each device, and comparison and analysis of the separate data can be unreliable if, for example, the data is not synchronized with regard to time, date or source. Still other systems do not allow for or adequately facilitate employment of separate measurement and administration devices independently of one another for the recordation and/or viewing of data. Thus, the user must employ the measurement and administration devices within the system to view the stored data for each device. Furthermore, systems employing multiple devices may not readily conceal that the devices are for medical treatment purposes, which can create embarrassment and inconvenience for the user.

Accordingly, there remains a need for additional systems and methods for measurement and treatment of bodily conditions which address these deficiencies, among others.

SUMMARY

According to one aspect, a diagnostic and medication delivery system includes a medication delivery pen including a controller; a monitor for monitoring a characteristic of a bodily fluid, the monitor including a controller; and a case including a compartment for removably storing each of the medication delivery pen and the monitor, the case including a communications link for establishing communication between the controller of the pen and the controller of the monitor.

In one embodiment, communication between the pen and monitor is disabled when one of the pen and monitor is removed from the compartment. In a further embodiment, the compartment is internal of the case.

According to another aspect, a diagnostic and medication delivery system includes a medication delivery pen including a controller; a monitor for monitoring a characteristic of a bodily fluid, the monitor including a controller; and a case including a compartment for removably storing the medication delivery pen and for removably storing the monitor within the case, the case including a communications link in the compartment configured to electrically connect the controller of the pen and the controller of the monitor when the pen and the monitor are positioned in the compartment.

In one embodiment, the pen includes at least one communications port and the monitor includes at least one communications port. Communication between the pen and monitor is established when the communications port of the pen is positioned in contact with the first electrical contact and at least one communications port of the monitor is positioned in contact with the second electrical contact.

According to another aspect, a kit is provided with a medication delivery pen including a controller; a monitor for monitoring a characteristic of a bodily fluid, the monitor including a controller; and a case including a compartment for removably storing the medication delivery pen and removably storing the monitor with the controllers in electrical communication with one another.

In one embodiment, the pen includes at least one communications port and the monitor includes at least one communications port. The case includes a data connection assembly including a first contact and a second contact. Electrical communication is established between the pen and the monitor with at least one communications port of the pen positioned in the compartment in contact with the first contact and at least one communications port of the monitor positioned in the compartment in contact with the second contact.

According to a further aspect, a device for storing a medication delivery pen and a monitor includes a case including a compartment, the compartment including a first portion for receiving the medication delivery pen and a second portion for receiving the monitor, the first and second portions including a data communications link extending therebetween for establishing communication between the pen and the monitor when the pen is placed in the first portion and the monitor is placed in the second portion.

These and other aspects will be further discussed below with reference to the illustrated embodiments.

DESCRIPTION OF THE ILLUSTRATED EMBODIMENTS

Figure 1:
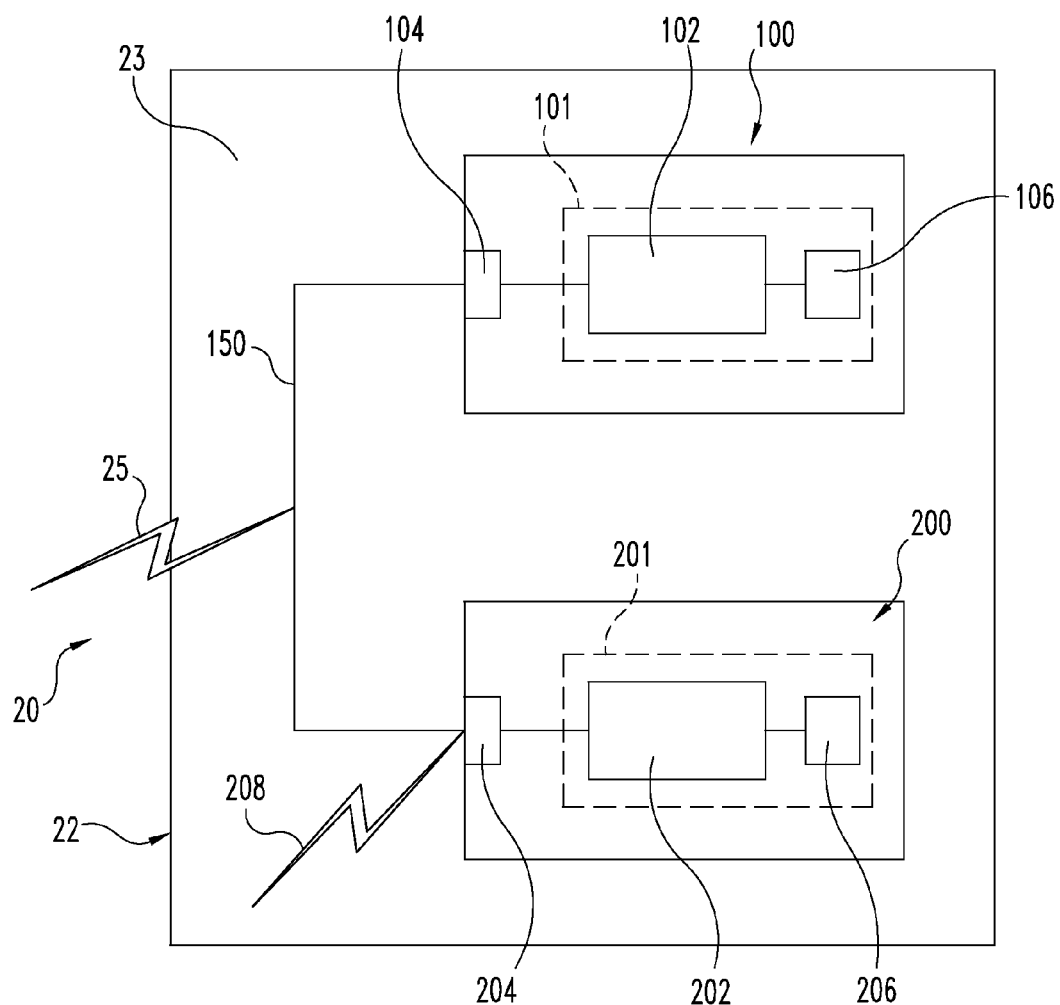
FIG. 1 is a schematic of a diagnostic and medication delivery system according to one aspect of the invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

According to one embodiment there is provided a system for delivery of diabetes treatment, such as insulin. The system includes a diabetes blood glucose monitor and medication delivery pen for insulin delivery in a convenient integrated system facilitating the management and treatment of diabetes. The pen and monitor each include a controller operable to record data relating to specific events associated therewith. For example, the pen controller can be programmed to measure and record data relating to one or more injection events. Such data may include the time, date and quantity of insulin injected by the pen. The monitor controller can be programmed to measure and record measurement event data. Measurement event data may include the time, date, blood characteristic, caloric intake and activity associated with one or more measurements. When employed in the system in a cooperative mode of operation, clock data associated with an injection event of the pen is synchronized with the clock of the controller of the monitor to reliably correlate the injection event data with the measurement event data.

The controller of the pen can be programmed to operate in a second stand-alone mode in which the clock data relating to an injection event is provided by the pen controller independently of the clock of the monitor. In the stand-alone mode the user can employ the pen independently and outside the system to obtain clock data for each injection. In the stand-alone mode the injection event data is not downloadable to the monitor since the clock data relating to the stored injection events has not been synchronized with the clock of the monitor.

A case is provided to conveniently and discretely store the pen and monitor for transport by the user. In one form, the case includes an exterior look of a case that is commonly carried on the person, such as a pen and pencil case, a make-up case, or an eyeglass case, for example. The case can be securely closed to conceal the pen and monitor in a compartment of the case, and can be readily opened to access the pen and monitor. The compartment is configured to securely retain the pen and monitor in respective receptacles within the compartment. The receptacles are coupled to one another with a communications link that establishes communication between the pen and monitor when the pen and monitor are placed in their respective portions of the compartment. When one of the pen and monitor are removed from the case, the communications link is interrupted.

The pen and/or monitor are removed from the case by the user in order to, for example, make an injection or measure a blood characteristic. The pen and monitor measure, receive and store data associated with the particular function for which it was employed. When the pen and monitor are each positioned in the case, a communication link is established between the pen and monitor. The injection event data is uploaded from the controller of the pen to the controller of the monitor. The controller of the monitor can function as a central controller. The centrally stored data on the monitor controller relating to the injection and measurement events can be maintained for review on a display of the monitor. The centrally stored data can also be uploaded from the monitor to a computer for display and analysis with appropriate software. Still further the multiple injection event data can be stored and viewed on the pen both before and after transfer to the monitor.

In FIG. 1 there is shown a schematic block diagram of a diagnostic and medication delivery system 20. System 20 includes a case 22 including a compartment 23 for removably storing a pen 100 and a monitor 200 therein in communication with one another. Pen 100 includes a controller 101 with memory 106 and a microprocessor 102. A communications port 104 is coupled to controller 101. Microprocessor 102 is programmable to process data input therein relating to an injection event and record the data in memory 106. Monitor 200 includes a controller 201 with a memory 206 and a microprocessor 202. A communications port 204 is coupled to controller 201. Microprocessor 202 is programmable to process data input therein relating to a measurement event and record the data in memory 206. Microprocessor 202 is further programmable to process injection event data received from memory 106 of pen 100 and record the injection event data in memory 206.

Controllers 101, 201 may each be comprised of one or more components configured as a single unit or of multi-component form. Controllers 101, 201 may each be programmable, a state logic machine or other type of dedicated hardware, or a hybrid combination of programmable and dedicated hardware. One or more components of controllers 101, 201 may be of the electronic variety defining digital circuitry, analog circuitry, or both. As an addition or alternative to electronic circuitry, controllers 101, 201 may include one or more mechanical or optical control elements.

In one embodiment including electronic circuitry, controllers 101, 201 each include an integrated processing unit 102, 202 operatively coupled to one or more solid-state memory devices defining, at least in part, memory 106, 206, respectively. For this embodiment, memory 106, 206 each contains programming to be executed by the respective processing units 102, 202 and is arranged for reading and writing of data in accordance with one or more routines executed by processing units 102, 202.

Memory 106, 206 each may include one or more types of solid-state electronic memory and additionally or alternatively may include the magnetic or optical variety. For example, memory 106, 206 each may include solid-state electronic Random Access Memory (RAM), Sequentially Accessible Memory (SAM) (such as the First-In, First-Out (FIFO) variety or the Last-In First-Out (LIFO) variety), Programmable Read Only Memory (PROM), Electrically Programmable Read Only Memory (EPROM), or Electrically Erasable Programmable Read Only Memory (EEPROM); or a combination of any of these types. Also, memory 106, 206 each may be volatile, nonvolatile or a hybrid combination of volatile and nonvolatile varieties.

Besides memory 106, 206, controllers 101, 201 may also each include any control clocks, interfaces, input devices, display device, signal conditioners, filters, limiters, Analog-to-Digital (A/D) converters, Digital-to-Analog (D/A) converters, communication ports, or other types of operators as would occur to those skilled in the art to implement the present invention.

Case 22 includes a data connection assembly 150 for connection with communication ports 104, 204 to establish communication between controllers 101, 201. In one embodiment, communications between pen 100 and monitor 200 can be established when both are positioned in compartment 23 with the respective communication ports 104, 204 in contact with data connection assembly 150. Data stored in memory 106 of pen 100 can be automatically transferred to controller 201 of monitor 200 when communication is established and upon satisfaction of certain validation conditions, which will be discussed further below. The pen memory data can be processed by processor 202 and stored in memory 206 of monitor 200.

Data from memory 206 of monitor 200, including data transferred from memory 106 of pen 100, can be uploaded to a computer or other device with a processor or microprocessor via communication link 208 for viewing and/or analysis. Alternatively or additionally, case 22 can include a communication link 25 coupled to communication port 204 of monitor 200 for transfer of data stored in memory 206 of monitor 200 to a third device. It is further contemplated that communication link 25 can be coupled to communication port 104 to transfer data from memory 106 of pen 100 to a third device.

Figure 2:
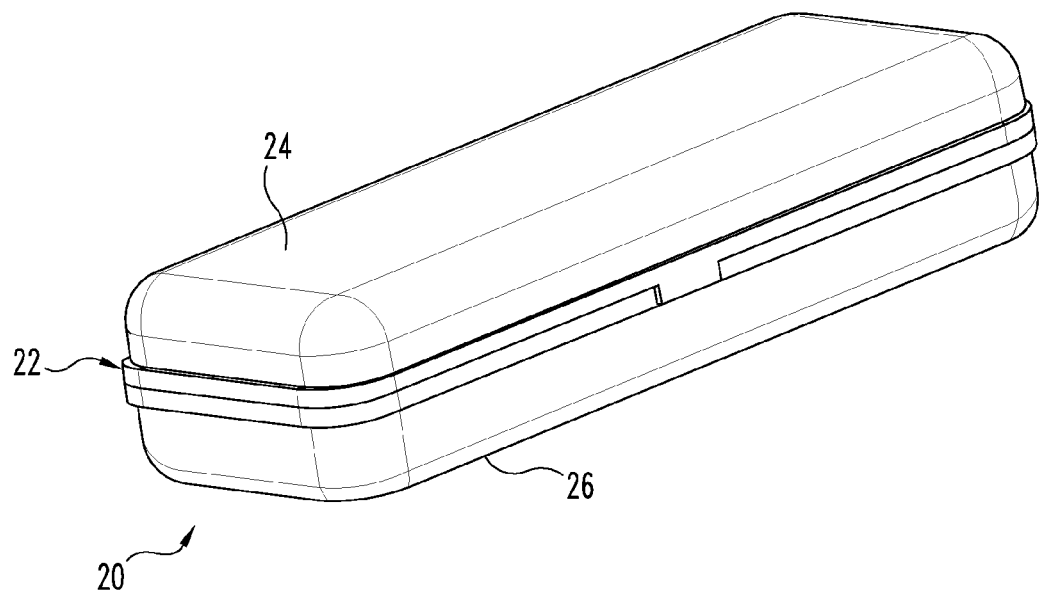
FIG. 2 is a perspective view of one embodiment of a case comprising a portion of the system of FIG. 1 in a closed configuration.
Figure 3:
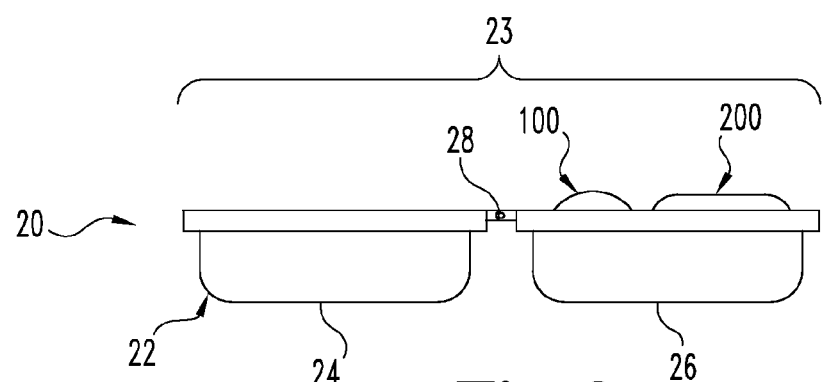
FIG. 3 is an end view of the case in FIG. 2 in an open configuration.
Figure 4:
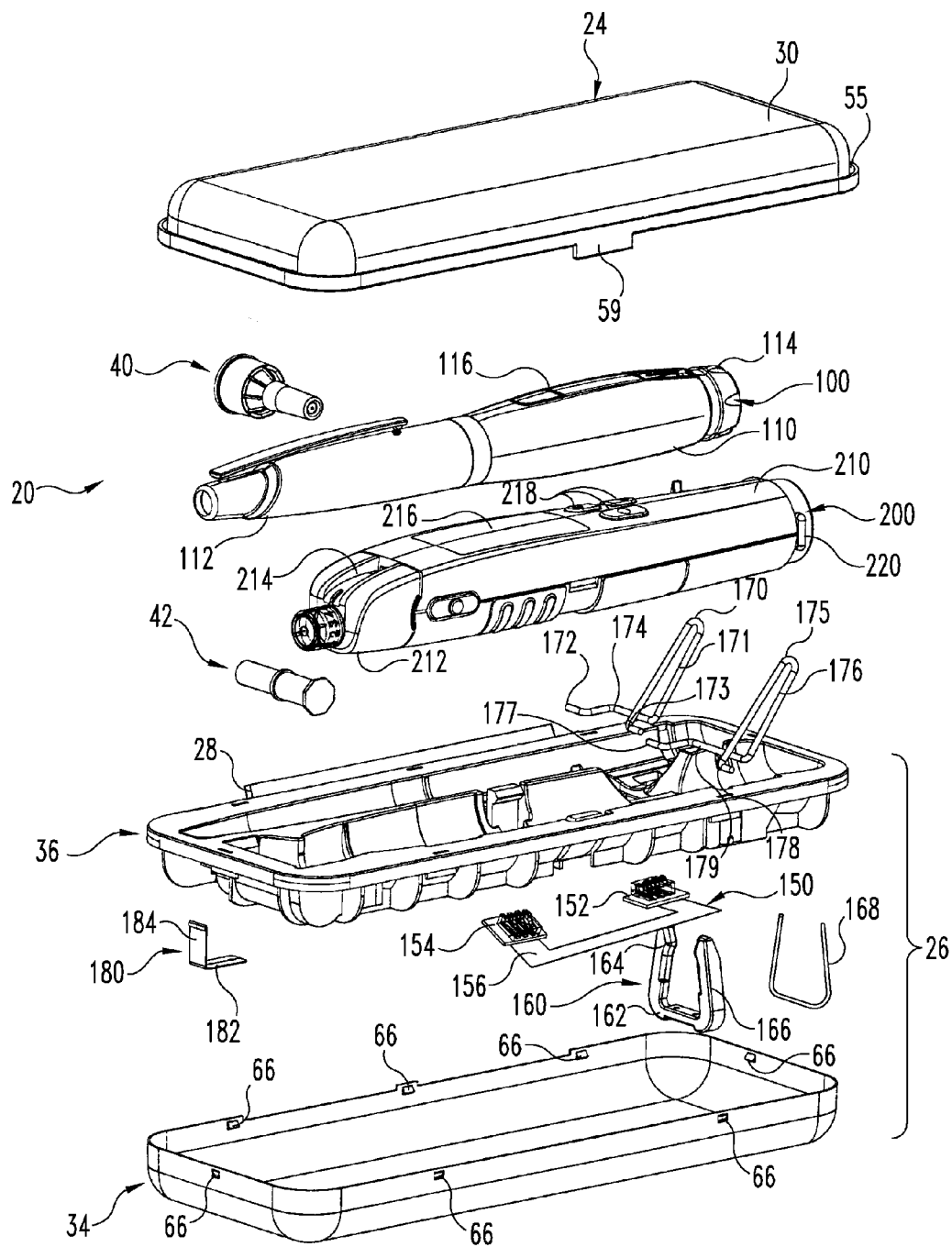
FIG. 4 is an exploded perspective view of one embodiment of the system of FIG. 1.

In FIGS. 2-4 there is shown one embodiment of diagnostic and medication delivery system 20 including case 22 with internal compartment 23. Case 22 includes a top member 24 hingedly coupled along one side thereof with an adjacent side of a bottom member 26. When case 22 is opened, as shown in FIG. 3, top member 24 can be pivoted 180 degrees about hinge mechanism 28 to provide access to pen 100 and monitor 200 positioned within compartment 23. When the case is closed, as shown in FIG. 2, the compartment and its contents are enclosed by top and bottom members 24, 26 to conceal the contents of case 22 and to protect the contents of case 22 from jarring, dropping or other physical abuse. Other embodiments contemplate that top member 24 and bottom member 26 can be configured to form any angle or position relative to one another, including disassembly, so long as the contents in compartment 23 are accessible.

Pen 100 and monitor 200 are removably stored in compartment 23 of case 22 between top member 24 and bottom member 26. It is contemplated that bottom member 26 includes a pair of compartment portions for securely retaining pen 100 and monitor 200 therein. Pen 100 is an insulin delivery pen with controller 101 operable to process and record data associated with one or more injection events. One example of an insulin delivery pen is described in PCT Publication No. WO 02/092153.

As shown in FIG. 4, pen 100 provides an overall appearance of an ink pen. Pen 100 includes a housing 110 and a cap assembly 112. A drive mechanism (not shown) is housed within housing 110 along with controller 101. An input and display system 116 is provided along housing 110 to provide push buttons, switches and displays for the user to input and view information to and from controller 101 and to turn pen 100 on or off. A dosing knob 114 is provided at one end of pen 100 adjacent housing 110 to provide a means to manually input dosing instructions to controller 101. An injection mechanism including a needle and cartridge (not shown) is operably coupled with the drive mechanism and positioned in cap assembly 112.

Monitor 200 is a blood glucose monitor with controller 201 operable to process and record data associated with a blood glucose measurement event. Monitor 200 includes a body portion 210 and a lancer 212. Lancer 212 can be storable within a receptacle of body portion 210, or integrated within body portion 210. It is further contemplated that monitor 200 can be provided without a lancer device. Body portion 210 houses controller 201 and includes a test strip interface 214. A test strip with a blood sample can be positioned in interface 214 and analyzed by monitor 200. The results can be displayed on display 216 and stored in memory 206. Input device 218 allows the user to enter or review data stored in memory 206 and turn monitor 200 on or off. A hinge 220 is provided to open and close a compartment in monitor 200 for internal storage of test strips or other items.

Case 22 further includes a data connection assembly 150 positioned therein for establishing a communications link between pen 100 and monitor 200 for transfer of data therebetween. Data connection assembly 150 includes a first contact 152, a second contact 154 and an electrical connector 156 therebetween. First contact 152 and second contact 154 are each in exposed in compartment 23 of case 22. When pen 100 is positioned in its proper location and orientation in the compartment, an electrical connection is made between a series of conductive pads on the pen exterior serving as communications port 104 of pen 100 and resilient brush-like elements of first contact 152. Similarly, when monitor 200 is positioned in its proper location and orientation in the compartment, an electrical connection is made between a series of conductive pads on the pen exterior serving as communications port 204 of monitor 200 and resilient brush-like elements of second contact 154. Electrical connector 156 transmits signals between controllers 101, 201 when the electrical connections with contacts 152, 154 are made. Data connection assembly 150 can be a hard-wired connection as shown, or can be a wireless interface, such as radio frequency link, an infrared link, or a Bluetooth link, for example.

Compartment 23 of case 22 can further be adapted to store and securely retain ancillary devices useful with pen 100 and/or monitor 200. For example, a pen needle 40 and a lancet 42 can be stored in case 22. Case 22 can further provide for the storage of other items in compartment 23, such as test strips, instructions, and lancer devices, for example.

Figure 5:
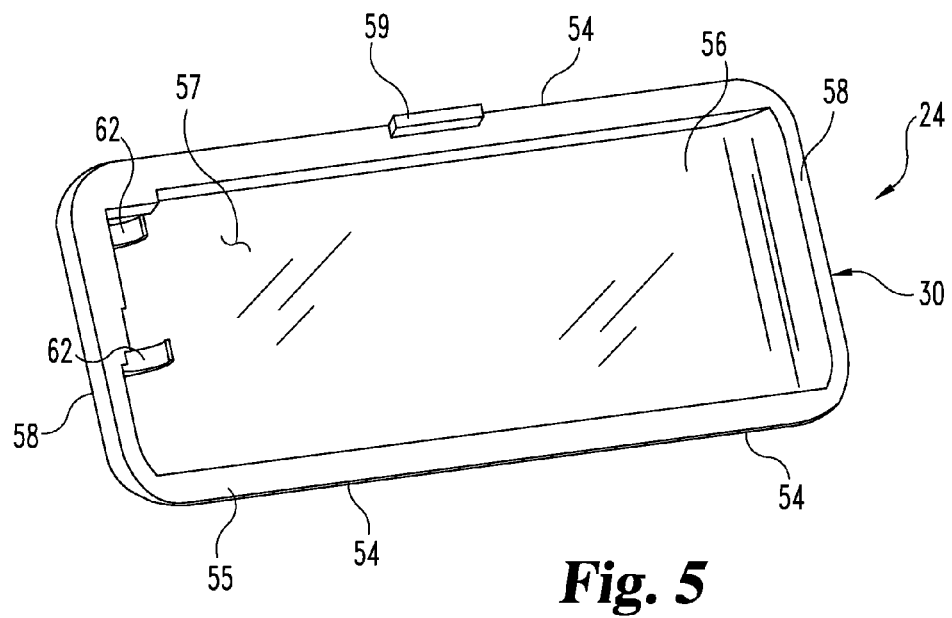
FIG. 5 is a perspective view of an upper portion of the case of FIG. 2.
Figure 6:
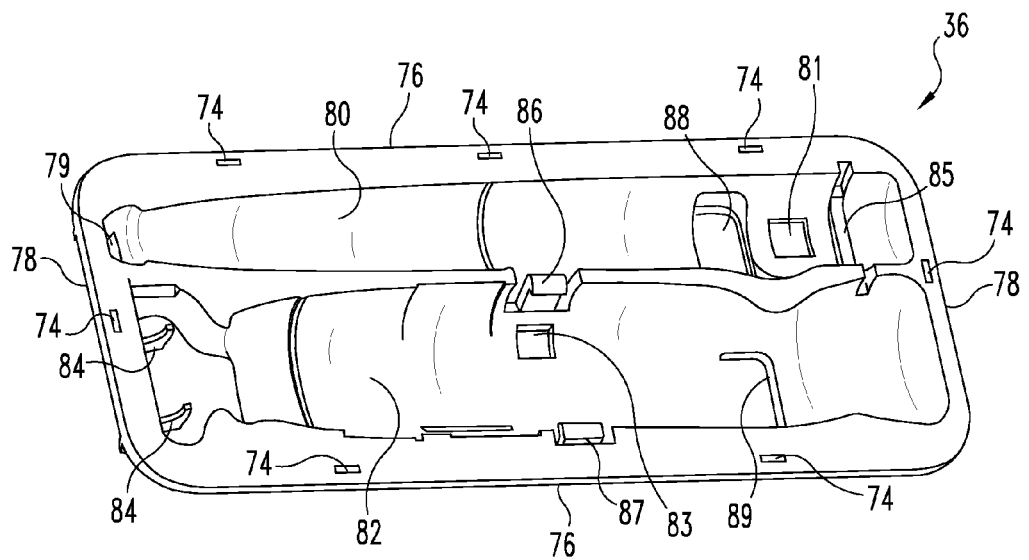
FIG. 6 is a perspective view of a lower portion of the case of FIG. 2.

Referring to FIGS. 4-6 further details with regard to case 22 will be discussed. Top member 24 and bottom member 26 can each be provided as an integral or one piece member, as shown in FIG. 4 with respect to top member 24. Alternatively, top member 24 and bottom member 26 can each be provided in one or more components, such as shown with respect to bottom member 26 in FIG. 4.

Top member 24 includes a body 30 having lip 55 extending therearound. As shown in FIG. 5, body 30 defines an upper compartment portion 57 orientable toward bottom member 26. In the illustrated embodiment, a latching mechanism 59 projects from lip 55 toward bottom member 26. Top member 24 is pivotally coupled to bottom member 26 opposite latching mechanism 59 along a hinge mechanism represented at 28. Hinge mechanism 28 can be provided in any suitable form for pivotally coupling top and bottom members 24, 26 to one another. One example includes one or more integral or living hinges between top and bottom members 24, 26. Another example includes alignable cylinder members extending from top and bottom members 24, 26 which receive and are rotatable about a rod extending through and interconnecting the cylinders. In yet another example, top and bottom members are not pivotally coupled to one another, but are slidable, movable, or otherwise displaceable from one another to access the compartment.

Latching mechanism 59 can be provided in any suitable form or device for releasably retaining top and bottom members 24, 26 in a closed position. Although one latching mechanism 59 is shown, multiple latching mechanisms 59 could be provided along one or more sides of top and bottom members 24, 26. In still another embodiment, no latching mechanisms are provided, and top and bottom members are biased to a closed position with a spring mechanism, magnetic mechanism, interfitting components that snap fit or releasably engage one another, or other suitable closing arrangement.

Top member 24 includes opposite longitudinal sidewalls 54 and a pair of opposite lateral sidewalls 58 extending between longitudinal sidewalls 54. Sidewalls 54, 58 extend about an upper compartment portion 56 and recessed wall 57. Wall 57 is recessed sufficiently to accommodate the portions of pen 100 and monitor 200 projecting upwardly from the compartment portions of bottom member 26 when case 22 is closed. A pen needle cradle 62 is formed along recessed wall 57 and is configured to hold pen needle 40 by frictional engagement, with the walls of the cradle extending about pen needle 40.

In the illustrated embodiment, bottom member 26 includes a lower skin 34 positionable about a lower liner 36 that forms a lower portion of compartment 23. Lower skin 34 can be comprised of a material that provides a rigid protective barrier to protect the contents placed in compartment 23. Materials contemplated include aluminum, stainless steel, plastic material, and other suitable materials and combinations of materials. It is further contemplated that top member 24 can be provided with a rigid outer protective barrier that is comprised of the same or differing material as the compartment portion 57.

Various means for securing liner 36 to its skin 34 are contemplated. For example, lower liner 36 can be provided with recesses 74 that align with protrusions 66 extending from lower skin 34 for a snap fit between lower skin 34 and lower liner 36. Other means for securing liner 36 to the skin 34 are also contemplated, including fasteners, adhesives, and fusion of the internal liner to the respective outer skin, for example.

Lower liner 36 includes opposite first and second longitudinal sidewalls 76, and a pair of opposite lateral sidewalls 78 extending between longitudinal sidewalls 76. Sidewalls 76, 78 extend about a lower compartment portion which includes a first compartment portion 80 and a second compartment portion 82. First compartment portion 80 is sized to accommodate pen 100 therein. Second compartment portion 82 is sized to accommodate monitor 200 therein. First and second compartment portions 80, 82 are shown in FIG. 6 with contours that correspond to the outer shape of the pen or monitor to be positioned therein. This prevents lateral movement or twisting of the pen and monitor in their respective compartment portions, and can also provide frictional engagement with lower liner 36 to assist in retaining pen 100 and monitor 200 in the respective compartment portions 80, 82. In other embodiments, first and second compartment portions 80, 82 can also be provided with contours that do not correspond to the outer shape of the pen and monitor to be positioned therein. A lancet cradle 84 is provided in a recess at one end of and adjacent to second compartment portion 82 to receive lancet 42 therein in frictional engagement with the wall portions of the cradle extending thereabout.

First compartment portion 80 includes a first data port opening 81 formed therethrough, and second compartment portion 82 includes a second data port opening 83 formed therethrough. First contact 152 of data connection assembly 150 is positioned in first data port opening 81 so that communications port 104 of pen 100 can be positioned thereon in electrical communication therewith. Similarly, second contact 154 of data connection assembly 150 is positioned in second data port opening 83 so that communications port 204 of monitor 200 can be positioned thereon in electrical communication therewith. Connector portion 156 extends between contacts 152, 154 positioned in data port openings 81, 83, and is located or housed between lower liner 36 and bottom skin 34 when assembled.

Lower liner 36 further includes clip receptacle 85 for receiving clip member 160 (FIG. 4) therein. Clip member 160 includes a bottom portion 162 and a pair of opposite resilient arms 164, 166 extending from and movable relative to bottom portion 162. Clip member 160 is positioned in clip receptacle 85 with arms 164, 166 extending upwardly therefrom to receive pen 100 therebetween. For example, arms 164, 166 can be received in a recess between knob 114 and housing 110. Arms 164, 166 move away from one another about an integral hinge at the connection of arms 164, 166 to bottom member 162 as pen 100 passes therebetween. Arms 164, 166 return toward their pre-pen insertion orientation when pen 100 is seated in first compartment portion 80 to grip pen 100 therebetween. A spring member 168 can be embedded in or positioned in a channel (not shown) formed in clip member 160 to maintain the gripping force of arms 164, 166 even after repeated insertion and removal of pen 100 from clip member 160.

Lower liner 36 further includes a pair of gripping members 86, 87 positioned on opposite sides of second compartment portion 82. Gripping members 86, 87 are movable about an integral hinge formed with lower liner 36. As monitor 200 is positioned in second compartment portion 82, gripping members 86, 87 move away from one another to accommodate insertion of monitor 200 therebetween. When monitor 200 is finally positioned in second compartment portion 82, gripping members 86, 87 return toward their pre-monitor insertion configuration and grip monitor 200 in second compartment portion 82.

Gripping members 86, 87 and clip member 160 securely retain monitor 200 and pen 100 in their respective compartment portions 82, 80. Such securement maintains the communication ports of the pen and monitor remain in electrical communication with the respective electrical contacts of data communication assembly 150, facilitating an uninterrupted data transfer from pen 100 to monitor 200 when each are positioned in case 22.

Lower liner 36 further includes slots 88, 89 to receive ejection levers 170, 175, (FIG. 4) respectively. Ejection lever 170 includes a handle member 171 and lower connection members 172, 173 extending transversely to handle member 171. Connection members 172, 173 are rotatably secured in openings (not shown) in the walls of lower liner 36 adjacent first compartment portion 80 and are movably received in slot 88. An ejection member 174 is positioned below pen 100 and, when unactuated, is recessed in slot 88 so that pen 100 can be fully seated in first compartment portion 80. When handle member 171 is manually raised, ejection member 174 is also raised from slot 88 and into contact with pen 100 to lift pen 100 out of first compartment portion 80 and out of engagement with clip member 160.

Similarly, ejection lever 175 includes a handle member 176 and lower connection members 177, 178 extending transversely to handle member 176. Connection members 177, 178 are rotatably secured in openings (not shown) in the walls of lower liner 36 adjacent second compartment portion 82 and are movably received in slot 89. An ejection member 179 is positioned below monitor 200 and, when unactuated, is recessed in slot 89 so that monitor 200 can be fully seated in second compartment portion 82. When handle member 176 is manually raised, ejection member 179 is also raised from slot 89 and into contact with monitor 200 to lift it out of second compartment portion 82 and between gripping members 86, 87.

A datum spring 180 (FIG. 4) can engage pen 100 when pen 100 is positioned in first compartment portion 80 to maintain communications port 104 in contact with first contact 152 of data connection assembly 150. Datum spring 180 includes an L-shaped body with a lower portion 182 mountable to the underside of lower liner 36, and an upper portion 184 extending through an opening 79 (FIG. 6) in lower liner 36. Opening 79 is in communication with first compartment portion 80 adjacent an end of pen 100. With pen 100 in first compartment portion 80, upper portion 184 of datum spring 180 pushes against the end of pen 100 to maintain an axial location of pen 100 in compartment portion 80. Datum spring 180 can also bias pen 100 downwardly into first compartment portion 80. Other embodiments contemplate that datum spring 180 is not provided, and pen 100 is maintained in the desired axial position in first compartment portion 80 with any one or combination of clip member 160 and the tolerances between pen 100 and the walls of lower liner 36 about first compartment portion 80.

It is contemplated that the material at least along the compartment portions housing the various devices includes sufficient rigidity to maintain structural integrity, and also sufficient elasticity and resiliency to accommodate the snap fit or frictional fit of the various devices therein without damaging the compartment portions or the outer surfaces of the devices. Suitable materials include plastics and polymers, for example.

In use, monitor 200 is removed from case 22 and employed to measure a blood characteristic. Other measurement event data associated with a measured blood characteristic can also be entered into controller 201 for storage in memory 206, such as whether the measurement event was associated with a meal, rest, or exercise. Pen 100 is removed from case 22 and employed by the user to make an insulin injection. With the pen powered on, the user can review injection event data stored in memory 106, dial the pen for injection of a dose, or prime the pen to prepare for an injection. Each prime event can be tagged by the user and stored in the memory 106 of pen 100. Other data associated with the injection event can be input and labeled in memory 106, such as whether the injection event was associated with a meal, rest, or exercise.

To display data stored in pen 100, it is contemplated that pen 100 includes a digital display coupled with controller 101 to display information, such as the date, time, dose reading, prime tags, battery life indicator, error information and indicators, and other information and indicators. It is further contemplated that pen 100 includes one or more data entry devices, such as push buttons, knobs, keypad or the like to facilitate user-initiated commands to controller 101. To display data stored in monitor 200, it is contemplated that monitor 200 includes a digital display coupled with controller 201 to display information, such as the date, time, blood glucose level, activity indicators, battery life indicator, error information and indicators, the data transferred from pen 100, and other information and indicators. It is further contemplated that monitor 200 includes one or more data entry devices, such as push buttons, knobs, keypad or the like to facilitate user entry of commands to controller 201.

The injection event data stored in memory 106 of pen 100 can be transferred to controller 201 of monitor 200 via data connection assembly 150 when pen 100 and monitor 200 are positioned in case 22 in their respective portions 80, 82 of compartment 23. In order to initiate and complete data transfer, the communication port 104 of pen 100 is placed in electrical engagement with first contact 152 of data connection assembly 150, and communication port 204 of monitor 200 is placed in electrical engagement with second contact 154 of data connection assembly 150.

Figure 7:
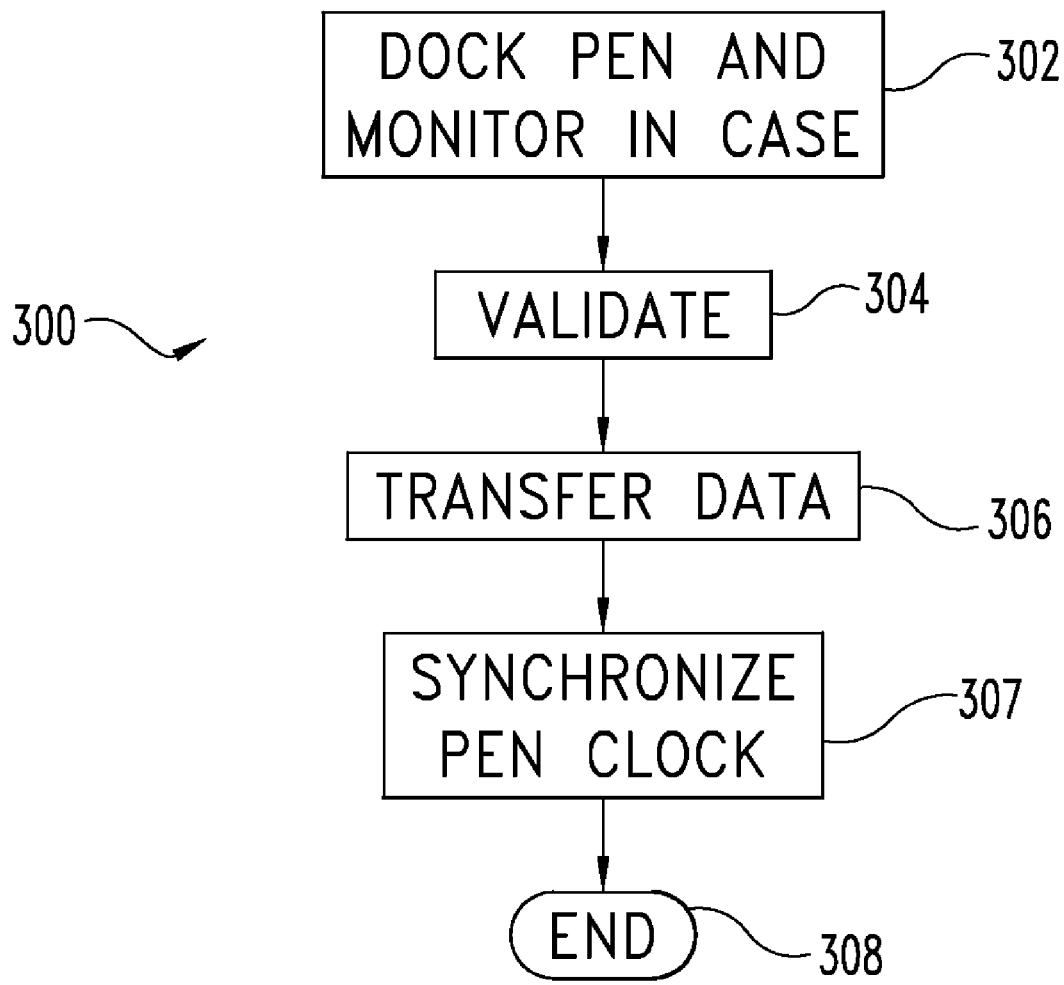
FIG. 7 is a flowchart of a routine programmable with the system of FIG. 1.

Referring to FIG. 7, a communications protocol for pen 100 and monitor 200 includes a routine 300 programmable in controller 101 of pen 100 and controller 201 of monitor 200 is shown. After completing one or more injection events with pen 100, pen 100 can be repositioned in case 22 and docked with data connection assembly 150, as indicated in stage 302. With pen 100 and monitor 200 docked in case 22, a communications protocol between pen 100 and monitor 200 is automatically initiated when pen 100 is operating in its cooperative mode. The communications protocol includes a validation test at stage 304. The validation test, as discussed further below, can include checking for connection between the pen and the monitor, and checking clock settings. The validation test can also include identifying and checking a serial number associated with pen 100. After validation of pen 100 and monitor 200, the data relating to the injection events, including prime events, stored in memory 106 of pen 100 are transferred via data connection assembly 150 to monitor 200 at stage 306. Transferred data can be marked to ensure that it is not re-transferred when pen 100 is removed from case 22 and re-docked therewith. When the data transfer is complete, the pen clock is synchronized with the monitor clock at stage 307. After synchronization, the pen and monitor each return to a standby or sleep mode at stage 308.

The injection event data transferred to and stored in memory 206 of monitor 200 can be accessed and reviewed on a display of monitor 200 along with the measurement date stored in memory 206 of monitor 200. It is further contemplated that the data stored in memory 206 of monitor 200 can be uploaded to a computer or a third device for reporting, analysis and/or processing purposes. Transferred injection event data can further be retained in memory 106 of pen 100 for subsequent viewing with pen 100 until overwritten by subsequent injection event data.

Figure 8:
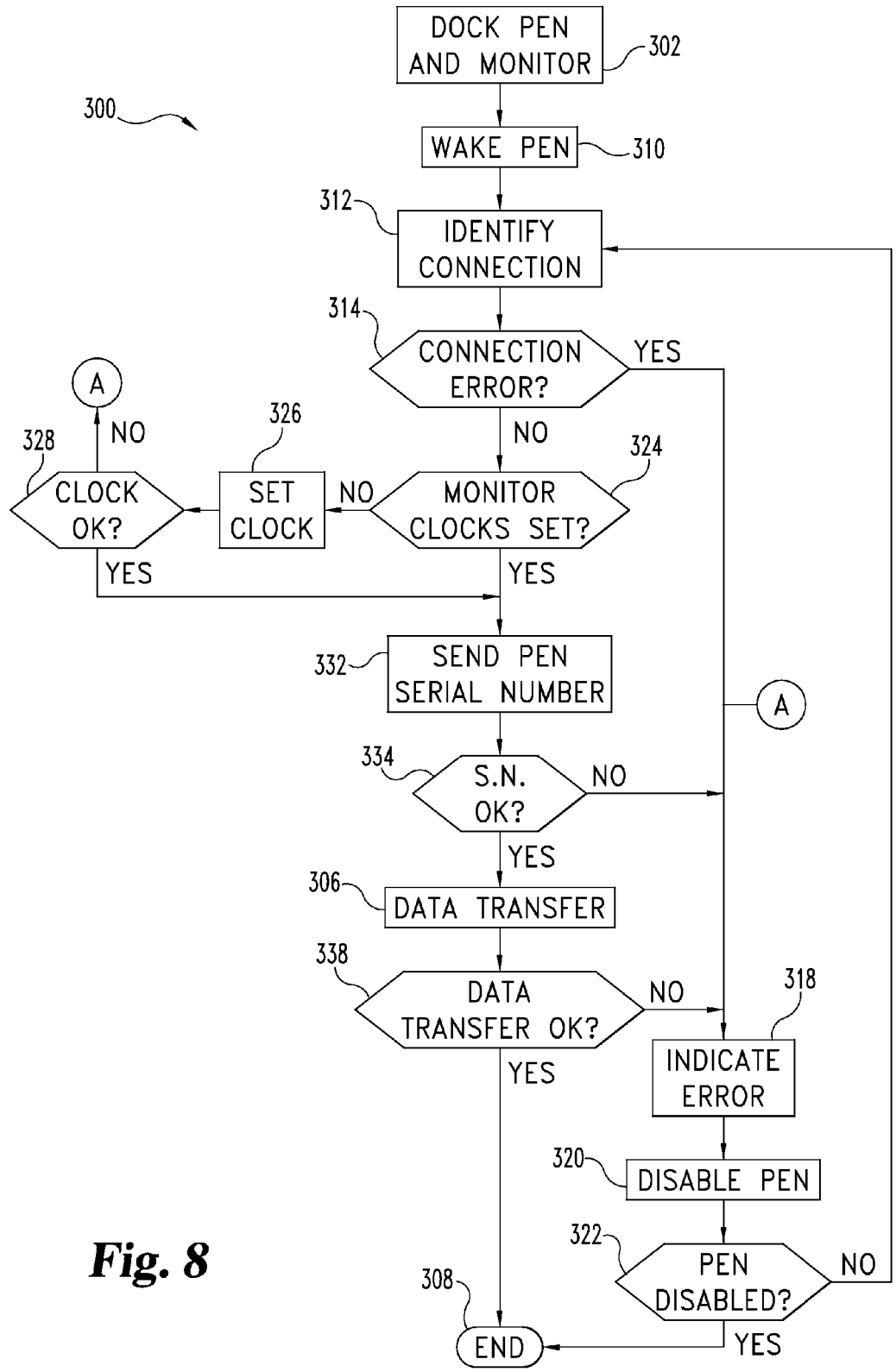
FIG. 8 is a flowchart of another embodiment of the routine of FIG. 7.

Further details with respect to the validation of pen 100 in routine 300 are provided in FIG. 8. Pen 100 is docked with case 22 at stage 302 with a serial low to high transition interrupt of controller 101 enabled after the last dose. At stage 310, if pen 100 is in a sleep mode when positioned in case 22, a signal is transmitted upon connection of communication port 104 of pen 100 with contact 152 of data connection assembly 150 to wake controller 101 of pen 100. At stage 312, pen 100 sends a pulse to monitor 200 through data connection assembly 150 to identify that pen 100 is docked in case 22 and connected with monitor 200. At stage 314 it is determined whether pen 100 is connected with monitor 200. If monitor 200 returns a signal to pen 100 through data connection assembly 150 to set the serial input to low, then the connection has been established and routine 300 continues at stage 324.

If at stage 314 it is determined that the serial input of pen 100 stays high, communication has not established between pen 100 and monitor 200 due to, for example, the lack of connection of one or both of pen and monitor with data connection assembly 150. The connection identification can be re-tried for a set number of retry attempts, such as three attempts. If a connection is not identified, an error indicator to the user is provided at stage 318. The error indicator can be any one or combination of an audible indication, a display message, or a lighted indicator on either or both of pen 100 and monitor 200. Once an error indication is made, the serial low to high transition interrupt of pen 100 is disabled at stage 320. If it is determined at stage 322 that the pen is not disabled due to, for example, communication between the pen and monitor being established by the user in view of the error indication at stage 318, then routine 304 returns to stage 312. If the pen 100 is disabled at stage 322, pen 100 returns to a standby or sleep mode at end stage 308.

If at stage 314 it is determined that the serial transition interrupt of pen 100 is set to low by monitor 200, then routine 300 continues at stage 324 to determine whether the monitor clock is set. At stage 324, monitor 200 determines whether a previous communication has been received from pen 100 that indicates the clock of pen 100 is synchronized with the clock of monitor 200. If so, routine 300 continues at stage 332. If there has not been any previous communication from pen 100 received by monitor 200, then monitor 200 checks to see if the clock of monitor 200 is set. If the monitor clock is set, then routine 300 continues at stage 332. If the monitor clock has not been set, then routine 300 continues at stage 326 where the clock of the monitor is initially set to correspond to the clock of pen 100. If it is determined at stage 328 that no errors in setting the monitor clock with the pen clock have occurred, then routine 300 continues at stage 332. If there is an error in setting the monitor clock with the pen clock, then after a set number of retry attempts routine 300 continues at stage 318 to provide an error indicator and continue as discussed above. Accordingly, the monitor clock can either be pre-set prior to use in system 200, or, if the pen clock has been set and the monitor clock is not set, then routine 300 initially sets the monitor clock to correspond to the pen clock.

At stage 332, pen 100 sends its serial number to monitor 200. If the serial number is recognized as valid at stage 334, then routine 300 continues at stage 306. If the serial number is not valid, and after a set number of retry attempts the serial number error persists, routine 300 continues at stage 318 to provide a serial number error indication. Recognition of a valid serial number of pen 100 ensures that pen 100 is properly programmed for communication with monitor 200. In addition, serial number identification can be used to stack and identify data from multiple pens 100 for storage in memory 206 of monitor 200.

After recognition of a valid serial number, untransferred injection event data stored in memory 106 of pen 100 can be transferred to monitor 200 at stage 306. It is contemplated that memory 106 of pen 100 can include data corresponding to multiple injection events, and that data associated with each event is transferred to monitor 200. When the injection event data is successfully transferred at stage 338, routine 300 ends at stage 308. If there is an error in transferring injection event data after a set number of retry attempts, then routine 300 continues at stage 318 to provide an error indicator and continues from stage 318 as discussed above.

Figure 9:
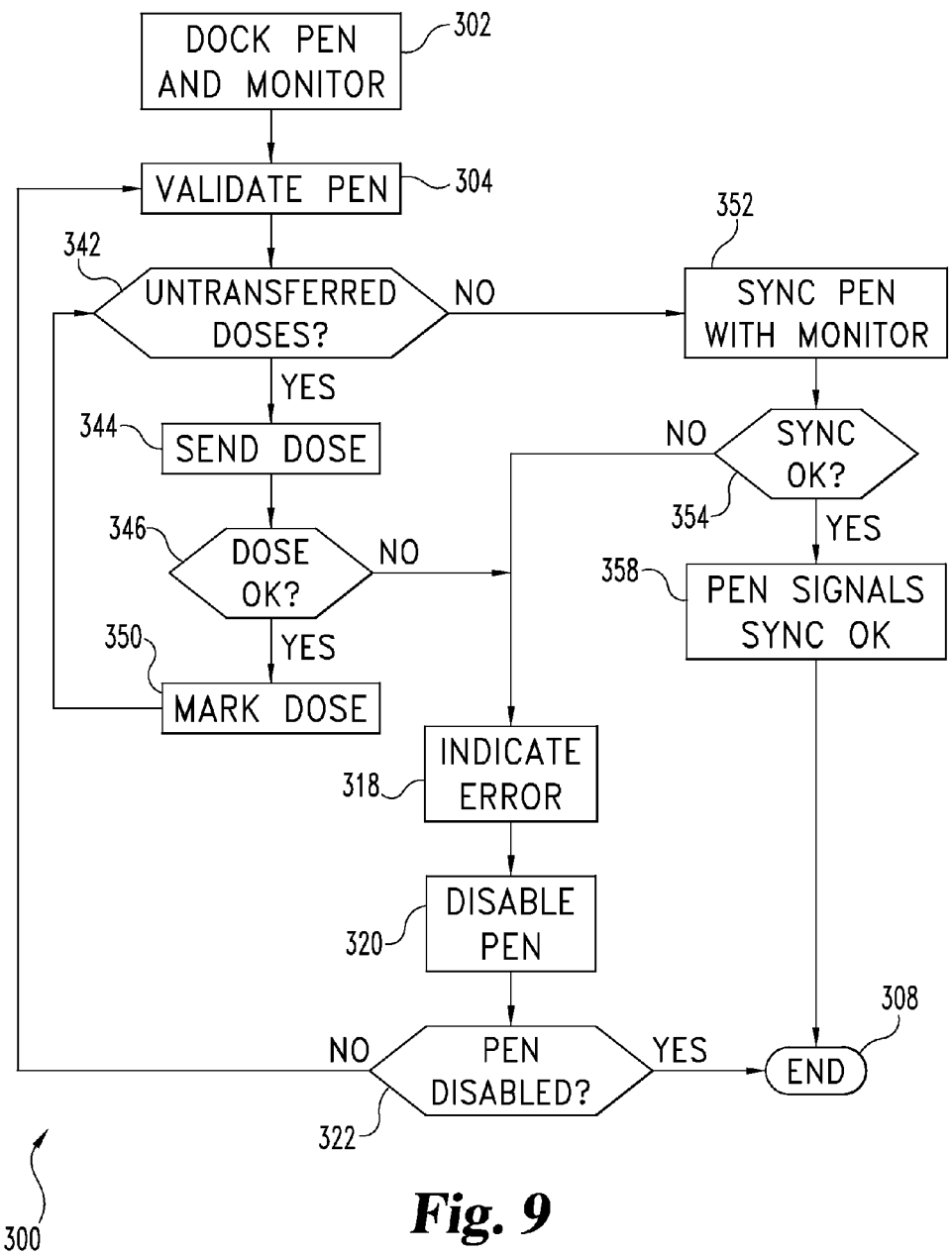
FIG. 9 is a flowchart of another embodiment of the routine of FIG. 7.

Referring to FIG. 9, there is shown additional details of data transfer stage 306 of routine 300. After validation of the pen at stage 304, pen 100 determines whether any untransferred dose or injection event data remain in memory 106 at stage 342. If untransferred injection event data is stored in pen 100 at stage 342, then routine 300 continues at stage 344 where the injection event data is transmitted to monitor 200. If the injection event data is not successfully transferred at stage 346 after set number of retries, then routine 300 continues to stage 318 to provide an error indicator and continues from stage 318 as discussed above.

If the injection event data is successfully transferred at stage 346, then routine 300 continues at stage 350 where the dose is marked as transferred. This allows dose or injection event data to remain stored in pen 100 for subsequent viewing with pen 100. However, the marked injection event data will be recognized as transferred data, preventing a subsequent transfer of the marked injection event data and expediting execution of routine 300. After marking the transferred injection event data, routine 300 returns to stage 342, where it is determined whether any untransferred injection event data is stored in memory 106 of pen 100. If so, then the next injection event data is transferred at stage 344, marked at stage 350, and routine 300 continues as discussed above. If not, then routine 300 continues from stage 342 to stage 352 to synchronize the pen clock with the monitor clock.

If all injection event data has been transferred, or if there were no untransferred injection event data, routine 300 synchronizes the clock of pen 100 with the clock of monitor 200 at stage 352. Pen 100 transmits a signal to monitor 200 indicating the pen 100 is ready to receive clock data from monitor 200. Monitor 200 sends the clock data to pen 100, which is checked at stage 354. If the transfer is successful and the clock data is synchronized, pen 100 signals to monitor 200 that the synchronization is complete, and pen 100 and monitor 200 return to a standby or sleep mode at stage 308. If the clock synchronization has not been successfully completed after a set number of retries, then routine 300 provides an error indicator at stage 318 and continues as discussed above.

It is contemplated that when pen 100 is operating in its cooperative mode that the validation, data transfer (if necessary) and clock synchronization are completed each time pen 100 is placed in case 22 with monitor 200. After transfer of unmarked injection event data to monitor 200, the clock of pen 100 is synchronized with the clock of monitor 200 to ensure a reliable and accurate comparison of data recorded with each device. Synchronization can include setting the time and date of the clock of pen 100 to correspond to the time and date of the clock of monitor 200. Synchronization of the clocks ensures that an accurate comparison of injection and prime event data can be made with the measurement event data stored in monitor 100. It is contemplated that once the clock in pen 100 is synchronized with the clock of monitor 200, the clock in pen 100 cannot be adjusted or changed by the user. This will ensure the recorded data of pen 100 and monitor 200 can be accurately and reliably compared and analyzed.

The injection event data remains stored in memory 106 of pen 100 even after transfer until over-written with a new injection event data. In one embodiment, pen 100 is capable of storing data for multiple injection events, including prime events. All, some or none of the injection event data stored in pen 100 may be marked as being transferred to monitor 200. Transferred and untransferred injection event data can be viewed with pen 100 in reverse chronological order, starting with the most recent injection event, and scrolled through by the user with an input device of pen 100.

Pen 100 and monitor 200 are each also operable in a stand-alone mode in which the clock of pen 100 is operable independently of monitor 200, and in which injection event data is not transferred from pen 100 when positioned in case 22 in communication with monitor 200. In one embodiment, pen 100 is operable in its stand-alone mode after a period of time elapses in which pen 100 is not positioned in communication with monitor 200. After the period of time elapses, the clock of pen 100 can be set independently by the user. This provides the user the flexibility to employ pen 100 and monitor 200 as stand-alone devices. In one embodiment, the pen converts to stand-alone mode automatically after a period of 14 days elapses without communication between pen 100 and monitor 200. It is contemplated that a warning indicator can be provided to provide an indication to the user prior to the pen converting to stand-alone mode. It is further contemplated that data stored in pen 100 while pen 100 is operating in the stand-alone mode can be flagged or marked so it is not downloaded to monitor 200.

While the invention has been illustrated and described in detail in the drawings and foregoing description, the same is to be considered as illustrative and not restrictive in character. All changes and modifications that come within the spirit of the invention are desired to be protected.

What is claimed is:

1. A diagnostic and medication delivery system, comprising:

a medication delivery pen including a controller;

a monitor for monitoring a characteristic of a bodily fluid, said monitor including a controller;

a case including a compartment for removably storing each of said pen and said monitor, said case including a communications link for establishing communication between said controller of said pen and said controller of said monitor when said pen and said monitor are stored in said compartment, said case includes a first member and a second member defining said compartment therebetween and movable relative to one another to open and close said case, wherein said first member and said second member each include a rigid outer skin and an internal liner, said compartment being defined between said internal liners of each of said first and second members, wherein said communications link includes a first contact in communication with a first compartment portion in one of said first and second members, a second contact in communication with a second compartment portion in said one of said first and second members, and an electrical connecter extending between said first contact and said second contact, said electrical connector being positioned between said liner and said outer skin of said one of said first and second members.

2. The system of claim 1, wherein said monitor includes a central controller.

3. The system of claim 1, wherein said monitor includes a lancer device.

4. The system of claim 1, wherein said communications link is a hard-wired connection extending between a first electrical contact and a second electrical contact in said compartment.

5. The system of claim 1, wherein one of said first and second members includes a first compartment portion for receiving said pen and a second compartment portion adjacent said first compartment portion for receiving said monitor.

6. The system of claim 5, wherein:
said communications link includes a first contact in said first compartment portion and a second contact in said second compartment portion;
said pen includes a communications port contactable with said first contact when said pen is positioned in said first compartment portion; and
said monitor includes a communications port contactable with said second contact when said pen is positioned in said second compartment portion.

7. The system of claim 6, wherein said case includes a clip member in said first compartment portion, said clip member including a pair of arms movable away from one another for insertion of said pen therebetween, said pair of arms being biased toward one another for engaging said pen in said first compartment portion and maintaining said communications port of said pen in contact with said first contact.

8. The system of claim 6, wherein said case includes a pair of gripping members on opposite sides of said second compartment portion, said gripping members being movable away from one another for insertion of said monitor in said second compartment portion, said gripping members being biased toward one another to engage said monitor in said second compartment portion and maintain said communications port of said monitor in contact with said second contact.

9. The system of claim 6, wherein said communications link includes an electrical connector extending between said first and second contacts.

10. The system of claim 1, wherein said first and second members are hingedly coupled to one another with a hinge mechanism along adjacent longitudinal sides of said first and second members.

11. The system of claim 10, wherein said case includes a latch mechanism opposite said hinge mechanism for securing said first and second members in a closed position.

12. The system of claim 1, wherein said communications link is structured to electrically connect said controller of said pen and said controller of said monitor when said pen and said monitor are positioned in said compartment.

13. The system of claim 12, wherein said communications link is a hard-wired connection extending between first and second electrical contacts located in said compartment.

14. The system of claim 1, wherein said compartment includes a first compartment portion adapted to removably engage said pen therein and a second compartment portion adjacent said first compartment portion adapted to removably engage said monitor therein.

15. The system of claim 14, wherein said first contact is located in said first compartment portion and said second contact is located in said second compartment portion.

16. The system of claim 1, further comprising a lancet device storable in said compartment.

17. The system of claim 1, further comprising a pen needle storable in said compartment.

* * * * *

UNITED STATES PATENT AND TRADEMARK OFFICE
CERTIFICATE OF CORRECTION

| | | |
|---|---|---|
| PATENT NO. | : 7,534,230 B2 | Page 1 of 1 |
| APPLICATION NO. | : 11/554138 | |
| DATED | : May 19, 2009 | |
| INVENTOR(S) | : Mark Follman | |

It is certified that error appears in the above-identified patent and that said Letters Patent is hereby corrected as shown below:

Col. 13, line 16, replace "connecter" with --connector--.

Signed and Sealed this

Thirtieth Day of June, 2009

JOHN DOLL
*Acting Director of the United States Patent and Trademark Office*